United States Patent [19]
Karlen et al.

[11] Patent Number: 6,042,819
[45] Date of Patent: *Mar. 28, 2000

[54] HAIR TREATMENT COMPOSITION WITH LONG-LASTING HAIR FIXING PROPERTIES

[75] Inventors: Thomas Karlen, Bern, Switzerland; Jürgen Schmenger, Weiterstadt, Germany; Silvia Borth, Fränkisch-Crumbach, Germany; Karin Steinbrecht, Ober-Ramstadt, Germany

[73] Assignee: Wella Aktiengesellschaft, Darmstadt, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/950,611

[22] Filed: Oct. 15, 1997

[30] Foreign Application Priority Data

Oct. 16, 1996 [DE] Germany .................. 196 42 622

[51] Int. Cl.$^7$ ........................................ A61K 31/74
[52] U.S. Cl. .................. 424/78.17; 424/70.1; 424/70.11; 424/70.12
[58] Field of Search ................ 424/78.17, 70.1, 424/70.11, 70.12

[56] References Cited

FOREIGN PATENT DOCUMENTS

93/23009  11/1993  WIPO .
95/03776   2/1995  WIPO .

*Primary Examiner*—Rebecca Cook
*Attorney, Agent, or Firm*—Michael J. Striker

[57] ABSTRACT

The hair treatment composition contains at least one nonionic, water-insoluble vinyl/silicone copolymer having a backbone chain of siloxane polymer units and a side chain of vinyl polymer units and at least one nonvolatile silicone derivative compound. Hair, which is treated with the composition according to the invention, has a long-lasting fixing effect, which lasts through several washings. The hair treated with the composition of the invention is flexible and has a natural feel.

12 Claims, No Drawings

HAIR TREATMENT COMPOSITION WITH LONG-LASTING HAIR FIXING PROPERTIES

BACKGROUND OF THE INVENTION

The subject matter of the present invention is a hair treatment composition containing at least one nonionic, water-insoluble vinyl/silicone copolymer with a backbone chain of siloxane polymer units and side chains of vinyl polymer units and at least one nonvolatile silicone derivative compound.

Hair treatment compositions with a hair fixing action are sufficiently well known. The conventional cosmetic polymers used for this purpose, which shape and fix the hair more or less well according to the application, have good fixing properties in aqueous or alcoholic solutions, but are washed out from the hair, at the latest, after shampooing it. Permanent shaping of the hair has been performed up to now only by chemical action on the hair structure action by means of a permanent shaping treatment.

Cosmetic compositions with a content of vinyl/silicone copolymers with a silicone backbone and acrylate side chains are described in WO 93/23009 and WO 95/03776. These polymers are nonionic, hydrophobic substances so that they are used in lip sticks, eye shadow pencils or antiperspirant sprays to obtain care effects. The vinyl/silicone copolymers are ionic hydrophilic substances so that they can also be used in hair sprays to obtain a hair fixing effect.

However no long-lasting fixing action is obtained because of the hydrophilicity of the ionic copolymers after several hair washings.

SUMMARY OF THE INVENTION

It is an object of the present invention to provide a hair treatment composition which fills the wide gap between a permanent wave treatment and a treatment with conventional hair fixing or hair sprays.

It is another object of the present invention to provide a hair treatment composition with long-lasting hair fixing action which does not leave the hair rigid and stick, but instead pliable and with a natural feel, without a visible residue and without damaging the hair by chemical action on the hair structure.

According to the invention, these objects are attained with a hair treatment composition containing (a) at least one nonionic, water-insoluble vinyl/silicone copolymer having a backbone chain of siloxane polymer units and a side chain of vinyl polymer units, and (b) at least one nonvolatile silicone compound.

The vinyl/silicone copolymer is present in the composition according to the invention preferably in an amount of from 0.1 to 50 percent by weight and the nonvolatile silicone compound preferably in an amount of from 0.01 to 50 percent by weight.

For example, suitable vinyl/silicone copolymer have the following general formula (I):

$$R^1R^2R^3Si\text{—}[O\text{-}SiR^4R^5\text{—}]_nO\text{—}SiR^6R^7R^8 \quad (I),$$

wherein the $R^1$ to $R^8$ groups are the same or different and, independently from each other, are each hydrogen, a hydroxy group, an alkyl group, an aryl group, an alkylaryl group, an alkoxy group, an alkylamino group, a fluoroalkyl group or a ZSA group, wherein Z represents a divalent connecting group, which is an alkylene group having from 1 to 10 carbon atoms, an alkarylene group having from 1 to 10 carbon atoms, an arylene group having from 1 to 10 carbon atoms or an alkoxyalkylene group having 1 to 10 carbon atoms, but is preferably methylene or propylene; S represents sulfur; A is a vinyl polymer segment built up from nonionic monomer groups and n is a number greater than or equal to 5; with the proviso that at least one of the $R^1$ to $R^8$ groups is one of the ZSA groups.

Suitable nonionic vinyl polymer segment monomers A are preferably esters of acrylic acid or methacrylic acid with alcohols having from 1 to 18 carbon atoms, especially from 1 to 12 carbon atoms. These ester are generally weakly polar and the short to moderate chain length alcohol makes the polymer substantially water-insoluble. Suitable alcohols are, e.g., ethanol, 1-propanol, 2-propanol, 1-butanol, 1,1-dimethylethanol, 2-methyl-1-propanol, 1-pentanol, 2-pentanol, 3-pentanol, 2-methyl-1-butanol, 3-methyl-1-butanol, 2-hexanol, 3-methyl-1-pentanol, cyclohexanol, 2-ethyl-1-butanol, 3-heptanol, benzyl alcohol, 2-octanol, 6-methyl-1-heptanol, 2-ethyl-1-hexanol, 3,5-dimethyl-1-hexanol, 3,5,5-trimethyl-1-hexanol, 1-decanol, 1-dodecanol and the like.

Small amounts of copolymerizable monomers, such as styrene, vinyl ester, vinyl chloride, vinylidene chloride, acrylonitrile, methacrylonitrile, acryloxypropyltrimethoxysilane, methacryloxypropyltrimethoxysilane, other aryloyl monomers and similarly structured monomers, can be used.

For example, particularly preferred monomers which can be added include isooctylmethacrylate, isononylmethacrylate, 2-ethylhexylmethacrylate, laurylmethacrylate, i-pentylmethacrylate, n-butylmethacrylate, i-butylmethacrylate, methylmethacrylate, ethylmethacrylate, t-butylmethacrylate, tridecylmethacrylate, stearylmethacrylate and similarly structured monomers and their mixtures.

Strongly polar, nonionic monomers can be copolymerized in small portions in the vinyl polymer segment A when the polymer according to the invention defined above remains substantially water-insoluble. For example, nonionic acrylate or methacrylate containing strongly polar, non-ionic monomers with at least one strongly polarizable group, such as hydroxyl, alkoxyl, an amino group(primary, secondary or tertiary) or an alkenyl heterocyclic, vinyl pyrrolidone or monomers with polyethylene oxide or polypropylene oxide side chains. The vinyl/silicone copolymer is however advantageously free of groups, which are present due to copolymerization of strongly polar, nonionic monomers in vinyl polymer segments A.

The vinyl polymer segment A of the vinyl/silicone copolymer is preferably free of anionic, cationic or amphoteric groups, which would reside therein by copolymerization of anionic, cationic or amphoteric monomers.

The vinyl/silicone copolymer according to the invention is made by a method described in WO 93/23009 and WO 95/03776.

Dimethylsiloxane/methyl-3-mercaptopropylsiloxane/isobutyl methacrylate copolymers (CFTA designation: Polysilicone-6) are particularly preferred as polymers for the hair treatment composition according to the invention.

A suitable product is, for example, sold under the tradename, Silicone "Plus" Polymer® VS 70 of 3M Corp., St. Paul, Minn., U.S.A.

Silicone derivative compounds with an evaporation number greater than 20 are what is meant by "nonvolatile silicone derivative compounds" for the purposes of this present invention. However silicone derivative compounds with an evaporation number of greater than 100 are particularly preferred. The evaporation number is defined as the quotient of the evaporation time of the tested liquid to the evaporation time of diethyl ether as comparison liquid.

The nonvolatile silicone derivative compounds have an upper limit for their viscosity of 100,000 mPa.s, but preferably of 20,000 mPa.s, at 25° C. Suitable nonvolatile silicone derivative compounds are, for example, high molecular weight polydimethylsiloxanes(dimethicones), polydimethylsiloxane with hydroxy end groups (Dimethiconols) or dimethylsiloxane glycol copolymers (dimethicone copolyols). Nonvolatile dimethylsiloxane glycol copolymers are, for example, sold under the trade names, Abil® Polyether-polysiloxane of Goldschmidt, Germany; Silwet®-L of Union Carbide, U.S.A. or silicone fluids 190, 193, Q2-5520 of Dow Corning, U.S.A.

Suitable nonvolatile silicone derivative compounds include also the cyclic siloxane polymers with an evaporation number greater than 100 such as those marketed under the trade name Dow Corning 244 or 245 Fluid of Down Corning, U.S.A., Abil® K4 of Goldschmidt, Germany or GE Silicone 1173 of GE Silicones, U.S.A.

The polydimethylsiloxanes with hydroxyl end groups (Dimethiconols) are particularly preferred silicone derivatives. Suitable Dimethiconols are, for example, sold under the trade name, silicone fluid F 212 or Silicone oil CT 601 M of Wacker, Germany; Silicone Fluid Series NM 201-5000 of Hüls, Germany, S-series of Siltech, U.S.A. and Unisil® SF-R of UPI, U.S.A. Suitable mixtures with volatile cyclomethicones or dimethicones include the commercial products Dow Corning Q2-1401 and Dow Corning Q2-1403 of Dow Corning, U.S.A. and Abil® OSW 12 and 13 of Goldschmidt, Germany.

A preferred embodiment of the hair treatment composition according to the invention includes at least one volatile silicone compound. A volatile silicone compound in the sense of the present invention means a silicone compound with an evaporation number of at most 20.

Suitable volatile silicone compounds include siloxane polymers such as those sold under the trade name Dow Corning 200 Fluid, Dow Corning 225 Fluid of Dow Corning, U.S.A.; Abil® 5000 of Goldschmidt, Germany or Belsil® DMC of Wacker, Germany.

Preferred embodiments of the hair treatment composition according to the invention can include at least one film-forming, hair-fixing, synthetic or natural polymer. These additional polymers can have anionic, cationic, amphoteric or nonionic character and preferably are present in an amount of from 0.01 to 50 percent by weight, particularly preferably from 0.5 to 50 percent by weight. Film-forming polymers are, for the purposes of this invention, those polymers which are used alone in 0.1 to 5% aqueous, alcoholic or aqueous-alcoholic solution under conditions in which a polymer film is deposited on the hair and the hair is fixed in this manner.

Suitable nonionic film-forming, hair-fixing polymers include, for example, homopolymers of vinylpyrrolidone, which are sold under the trade name, Luviskol® K by BASF AG, Ludwigshafen, Germany or PVP-K of ISP, Wayne, N.J., U.S.A. and homopolymers of N-vinylformamides, such as those sold under the trade name PVF of National Starch, U.S.A. Additional suitable nonionic film-forming, hair-fixing polymers include copolymerizates of vinylpyrrolidone and vinyl acetate, which, e.g., are sold under the trade name, Luviskol® VA, by BASF AG, Ludwigshafen, Germany; terpolymers of vinyl pyrrolidone, vinyl acetate and vinyl propionate, which, e.g., are sold under the tradename, Luviskol® VAP, by BASF AG, Ludwigshafen, Germany; polyacrylamide, which for example is sold under the trade name, Akypomine® P191 of CHEM-Y, Emmerich, Germany or Sepigel® 305 of Seppic, U.S.A; polyvinyl alcohols, which for example are marketed under the trade name, Elvanol® of DuPont or Vinol® 523/540 of Air Products, U.S.A. and polyethylene glycol with a molecular weight of from 800 to 20,000 g/mol, which is marketed for example under the trade name, Lipoxol® 1000 of Hüls AG, Germany; Pluracol E 4000 of BASF, Germany or Upiwax® 20,000 of UPI.

Suitable synthetic film-forming anionic polymers include, e.g., crotonic acid-vinyl acetate copolymers, which for example are sold in the form of a 60 percent solution in isopropanol/water under the trade name, Aristoflex® of Hoechst, Germany. Additional suitable anionic polymers include, for example, terpolymers of acrylic acid, ethyl acrylate and N-t-butylacrylamide, such as those sold under the trade name, Ultrahold 8 and Ultrahold Strong of BASF, Ludwigshafen, Germany.

Suitable natural film-forming polymers with hair fixing action, for example, include low molecular weight Chitosan with a molecular weight of from 30,000 to 70,000 g/mol, which for example is marketed by Kyowa Oil & Fat, Japan. Also different saccharide types can be used, such as polysaccharides or mixture of oligo-, mono- and disaccharides, which are sold under the trade name C-PUR® of Cerestar, Brüssels, Belgium. Additional suitable natural polymers include Chinese balsam resin and cellulose derivative compounds, such as hydroxypropyl cellulose with a molecular weight of from 30,000 to 50,000 g/mol, which is marketed under the trade name NISSO SL® of Lehmann & Voss, Hamburg, Germany.

Suitable amphoteric polymers include for example copolymers of octylacrylamide, t-butylaminoethylmethacrylate and two or more monomers selected from the group consisting of acrylic acid, methacrylic acid or their esters, such as those obtainable from National Starch, U.S.A., under the trade names, Amphomer® 28-4910 and Amphomer® LV-71.

Suitable cationic polymers for the hair treatment composition according to the invention include polyvinylpyrrolidone/dimethylaminoethylmethacrylate copolymer, such as sold under the trade name, Gafquat® 755N of Gaf Co., New York, U.S.A. Additional cationic polymers are, for example, the copolymers of polyvinylpyrrolidone and imidazoliminmethochloride, marketed under the trade name, Luviquat® HM 550 by BASF AG, Ludwigshafen, Germany; the terpolymer of dimethyldiallylammonium chloride, sodium acrylate and acrylamide, marketed under the trade name Merquat® Plus 3300 of Calgon, Pittsburgh, U.S.A.; the terpolymer of vinylpyrrolidone, dimethylaminoethylmethacrylte and vinylcaprolactam, sold by ISP, U.S.A. under the trade name Gaffix® VS 713; the quaternary ammonium salt of hydroxyethyl cellulose and a trimethylammonium-substituted epoxide, marketed under the trade name Polymer JR® of Amercol, Edison, U.S.A.; vinylpyrrolidone/methacrylamidopropyltrimethylammonium chloride copolymer marketed under the trade name, Gafquat® HS 100 by Gaf, and diquaternary polydimethylsiloxane marketed under the trade name, Abil® Quat 3272 of Goldschmidt, Germany.

Polymers with thickening action can also be contained in the hair treatment composition of the invention. These thickeners can include, for example, homopolymers of acrylic acid with a molecular weight of from 2,000,000 to 6,000,000, which, e.g., are sold by BF Goodrich, Cleveland, U.S.A. under the trade name, Carbopol®. An acrylic acid homopolymer with a molecular weight of 4,000,000 can be used in the composition of the invention as an additional thickener, which for example is sold by BF Goodrich, Cleveland, U.S.A. under the trade name, Carbopol® 940. Additional thickeners which can be used in the hair treatment composition according to the invention include acrylic acid homopolymers which for example are sold under the trade names of Carbopol® ETD 2001 by BF Goodrich, Cleveland, U.S.A. or under the trade name Modarez V 600 PX by Protex, France; polymers made from acrylic acid and acrylamide (sodium salt), sold under the trade name, Hostacerin® PN 73 by Hoechst, Germany, with a molecular weight of 2,000,000 to 6,000,000, and sclerotium gum, sold by the firm of Alban Muller, Montreuil, France, under the trade name Amigel®.

Additional thickeners which are especially preferred include the copolymers of acrylic acid or methacrylic acid, such as those sold under the trade name Carbopol 1342 or Pemulen TR1 of Goodrich, U.S.A.

The composition according to the invention is preferably packaged in an alcoholic or in an aqueous-alcoholic media, however it is also possible to provide a water-free formulation of it. Furthermore solvents or mixtures of solvents with a boiling point under 400° C. in an amount of from 0.5 to 90 percent by weight, preferably from 5 to 50 percent by weight. Straight chain non-branched or branched hydrocarbons, such as pentane, hexane, isopentane and cyclic hydrocarbons, such as cyclopentane and cyclohexane, are particularly preferred.

Lower alcohols suitable for cosmetic purposes, such as alcohols with 1 to 4 carbon atoms, such as ethanol and isopropanol, can also be contained as alcohols in the composition according to the invention.

Understandably the hair treatment composition according to the invention can contain conventional cosmetic additive ingredients, such as non-fixing, nonionic polymers, for example polyethylene glycol with a molecular weight of 600 g/mol; non-fixing, anionic polymers and non-fixing, natural polymers as well as their combinations in an amount of preferably from 0.01 to 50 percent by weight; perfume oils in an amount of preferably from 0.01 to 5 percent by weight; turbidity inducing agents, such as ethyleneglycoldistearate, in an amount of advantageously from 0.01 to 5 percent by weight; wetting agents or emulsifiers from the classes of anionic, cationic, amphoteric or nonionic surfactant compounds without detergent effect, such as fatty alcohol sulfates, ethoxylated fatty alcohols, fatty acid alkanolamides, such as esters of hydrogenated castor oil fatty acids, in an amount of preferably from 0.1 to 30 percent by weight; moisturizing agents; dye compounds; light protective agents; antioxidants; luster imparting agents and preservative substances, in an amount of preferably from 0.01 to 10 percent by weight.

The composition according to the invention can be in different application forms, for example an aerosol preparations such as a foam or spray, or a non-aerosol preparation, which is applied by means of a pump or as a "pump and spray" preparation. The composition can be provided as a conventional O/W and W/O emulsion as well as a gel, wax or microemulsion.

The composition according to the invention can be formulated as a hair dyeing hair treatment composition, a hair care composition or a hair tinting, fixing and rinsing composition.

When the composition according to the invention is in the form of a aerosol hair spray or aerosol hair lacquer, it contains a propellant in an amount of from 15 to 85 percent, preferably from 25 to 75 percent and is filled in a pressurized container.

Lower alkanes, for example n-butane i-butane and propane, or also their mixtures with dimethyl ether and gaseous form propellants, such as $N_2$, $N_2O$ and $CO_2$ and their mixtures are suitable as the propellant.

The composition according to the invention for fixing hair can also be sprayed in the form of a suitable non-aerosol hair spray or a non-aerosol hair lacquer with the help of a suitable mechanically operated spraying device.

By "mechanical spraying device" devices are to be understood, which allow spraying of a liquid with use of a propellant. These suitable mechanical spraying devices can, for example, be a spray pump or an elastic container provided with a spray valve. The composition according to the invention is filled in the elastic container under pressure so that the elastic container is expanded and then, when the spray valve is opened, the composition is dispensed because of contraction of the elastic container.

By "hair treatment" a treatment of human hair, above all, for the purposes of care of the hair or making a hair style is to be understood.

Furthermore the polymer combination according to the invention allows the preparation of concentrates with reduced water content or solvent content. The concentrates are then converted into the ready-to-use hair treatment composition by addition of the required amount of water or solvent after transportation and storage.

Washout tests in combination with a measurement of curl retention show that hair which is treated with the hair treatment compositions of the invention, even after washing with conventional shampoos, shows a notable fixing effect without damage to the hair. After many washings the fixing effect is still retained on the treated hair. The hair treated with the composition according to the invention is pliable and has a natural feel.

The following examples should illustrate the composition according to the invention.

| EXAMPLES | |
|---|---|
| Example 1: | Liquid Fixing composition with Long-lasting Fixing Effect |
| 6.0 g | Dimethylsiloxane/Methyl-3-mercaptopropyl-siloxane/Isobutylmethacrylate Copolymer |
| 50.0 g | Cyclooctamethyltetrasiloxane |
| 5.0 g | Vinylpyrrolidone/Vinylacetate Copolymer |
| 2.0 g | Dihydroxypolydimethylsiloxane, 12% in Cyclodimethyisiloxane (Abil ® OSW 12 of Goldschmidt/Germany) |
| 37.0 g | Pentane |
| 100.0 g | |
| Example 2: | Foam Fixing Composition with Long-lasting Fixing Effect |
| 4.0 g | Dimethylsiloxane/Methyl-3-mercaptopropyl-siloxane/Isobutylmethacrylate Copolymer |
| 20.0 g | Cyclooctamethyltetrasiloxane |
| 20.0 g | Polydimethylsiloxane (Dow Corning 200 Fluid of Dow Corning/USA) |
| 5.0 | Dimethiconol, 13% in Cyclopolydimethylsiloxane (Dow Corning 1401 Fiuid of Dow Corning/USA) |
| 5.0 g | Vinylpyrrolidone/Vinylacetate Copolymer |
| 0.2 g | Cetyltrimethylammonium chloride |

| | |
|---|---|
| 45.8 g | Isopropanol |
| 100.0 g | |
| Example 3: | Spray Fixing Composition with Long-lasting Fixing Effect |
| 3.0 g | Dimethylsiloxane/Methyl-3-mercaptopropyl-siloxane/Isobutylmethacrylate Copolymer |
| 2.0 g | Dimethiconol in Cyclopolydimethylsiloxane (Dow Corning Fluid 1403 of Dow Corning/USA) |
| 2.0 g | Octylacrylamide/Acrylate/Butylaminoethyl-methacrylate Copolymer |
| 0.5 g | Cetyltrimethylammonium chloride |
| 92.5 g | Isopropanol |
| 100.0 g | |
| Example 4: | Hair Cream for Fixing with Long-lasting Fixing Effect |
| 5.0 g | Dimethylsiloxane/Methyl-3-mercaptopropyl-siloxane/Isobutylmethacrylate Copolymer |
| 50.0 g | Cyclooctamethyltetrasiloxane |
| 2.0 g | Acrylate/Alkylacrylate Copolymer (Pemulen TR1 of BF Goodrich Co./USA) |
| 1.0 g | Dihydroxypolydimethylsiloxane, 13% in Cyclo-dimethylsiloxane (Abil ® OSW 13 of Goldschmidt/Germany) |
| 5.0 g | Water |
| 37.0 g | Isopropanol |
| 100.0 g | |
| Example 5: | Liquid Dye Composition with Long-lasting Fixing Effect |
| 4.0000 g | Dimethylsiloxane/Methyl-3-mercaptopropyl-siloxane/Isobutylmethacrylate Copolymer |
| 50.0000 g | Cyclooctamethyltetrasiloxane |
| 0.5000 g | Dimethiconol (Silicone Fluid F 212 of Wacker/Germany) |
| 0.0700 g | 1-Amino-4-(2,3-dihydroxypropyl) amino-5-chloro-2-nitrobenzene |
| 0.0500 g | Basic Brown 17 (C.I. 12251) |
| 0.0023 g | Basic Violet 14 (C.I. 42595) |
| 0.0100 g | Basic Blue 7 (C.I. 42595) |
| 20.0000 g | Pentane |
| 25.3677 g | Propanol |
| 100.0000 g | |
| Example 6: | Foam Fixing-concentrate with Long-lasting Fixing Effect |
| 10 g | Dimethylsiloxane/Methyl-3-mercaptopropyl-siloxane/Isobutylmethacrylate Copolymer |
| 50 g | Cyclooctamethyltetrasiloxane |
| 10 g | Dimethiconol(Silicone Fluid F 212 of Wacker/Germany) |
| 2 g | Cetyltrimethylammonium chloride |
| 6 g | Acrylic acid/Ethylacrylate/N-tert.-Butyl-acrylamide Copolymer |
| 22 g | Pentane |
| 100 g | |
| Example 7: | Hair spray with Long-lasting Fixing Effect |
| 5.0 g | Dimethylsiloxane/Methyl-3-mercaptopropyl-siloxane/Isobutylimethacrylate Copolymer |
| 44.5 g | Cyclooctamethyltetrasiloxane |
| 0.5 g | Dimethiconol (Silicone Fluid F 212 of Wacker/Germany) |
| 5.0 g | Vinylpyrrolidone/Vinylacetate Copolymer |
| 10.0 g | Pentane |
| 35.0 g | Propane/Butane |
| 100.0 g | |
| Example 8: | Liquid Fixing Composition with Long-lasting Fixing Effect |
| 6.0 g | Dimethyisiloxane/Methyl-3-mercaptopropyl-siloxane/Isobutylmethacrylate |
| 50.0 g | Cyclooctamethyltetrasiloxane |
| 2.0 g | Dimethicone Copolyol (Abil ® B 88183 of Goldschinidt/Germany) |
| 5.0 g | Vinylpyrrolidone/Vinylacetate Copolymer |
| 37.0 g | Pentane |
| 100.0 g | |
| Example 9: | Foam Fixing Composition with Long-lasting Fixing Effect |
| 4.0 g | Dimethylsiloxane/Methyl-3-mercaptopropyl-siloxane/Isobutylmethacrylate |
| 20.0 g | Cyclooctamethyltetrasiloxane |
| 20.0 g | Dimethicone (Abil ®10000 of Goldschmidt/Germany) |
| 5.0 g | Dimethicone Copolyol (Abil ® B 88184 of Goldschmidt/Germany) |
| 5.0 g | Vinylpyrrolidone/Vinylacetate/Vinylpropionate Copolymer |
| 0.2 g | Cetyltrimethylammonium chloride |
| 45.8 g | Isopropanol |
| 100.0 g | |
| Example 10: | Spray Fixing Composition with Long-lasting Fixing Effect |
| 3.0 g | Dimethylsiloxane/Methyl-3-mercaptopropyl-siloxane/Isobutylmethacrylate |
| 2.0 g. | Dimethicone (Abil ® 10000 of Goldschmidt/Germany) |
| 2.0 g | Octylacrylamide/Acrylate/Butylaminoethyl-methacrylate Copolymer (Amphomer LV 71 of National Starch/USA) |
| 0.5 g | Cetyltrimethylammonium chloride |
| 92.5 g | Isopropanol |
| 100.0 g | |
| Example 11: | Hair Cream for Fixing with Long-lasting Fixing Effect |
| 5.0 g | Dimethylsiloxane/Methyl-3-mercaptopropyl-siloxane/Isobutylmethacrylate |
| 50.0 g | Cyclooctamethyltetrasiloxane |
| 1.0 g | Dimethicone (Abil ® 10000 of Goldschmidt/Germany) |
| 2.0 g | Acrylate/C10-30 Alkylacrylate Crosspolymer (Pemulen TR-1 of Goodrich/USA) |
| 5.0 g | Water |
| 37.0 g | Isopropanol |
| 100.0 g | |
| Example 12: | Liquid Dye Composition with Long-lasting Fixing Effect |
| 4.0 g | Dimethylsiloxane/Methyl-3-mercaptopropyl-siloxane/Isobutylmethacrylate |
| 50.0 g | Cyclooctamethyltetrasiloxane |
| 0.5 g | Dimethicone Copolyol (Abil ® B 88184 of Goldschmidt/Germany) |
| 0.0700 g | 1-Amino-4-(2,3-dihydroxypropyl)amino-5-chloro-2-nitrobenzene |
| 0.0500 g | Basic Brown 17 (CI 12251) |
| 0.0023 g | Basic Violet 14 (CI 42510) |
| 0.0100 g | Basic Blue 7 (CI 42595) |
| 20.0 g | Pentane |
| ad | Propanol |
| 100.0 g | |
| Example 13: | Foam Fixing-Concentrate with Long-lasting Fixing Effect |
| 10.0 g | Dimethylsiloxane/Methyl-3-mercaptopropyl-siloxane/Isobutylmethacrylate |
| 50.0 g | Cyclooctamethyltetrasiloxane |
| 10.0 g | Dimethicone Copolyol (Abil ® B 88183 of Goldschmidt/Germany) |
| 6.0 g | Acrylate/Acrylamide Copolymer (Ultrahold 8 of BASF/Germany) |
| 2.0 g | Cetyltrimethylammonium chloride |
| 22.0 g | Pentane |
| 100.0 g | |

Unless otherwise indicated, all percents are in percent by weight.

The disclosure in German Patent Application 19642622.7 of Oct. 16, 1996 is incorporated here by reference. This German Patent Application, at least in part, describes the invention described hereinabove and claimed in the claims appended herein in below and provides the basis for a claim of priority for the instant invention under 35 U.S.C. 119.

While the invention has been illustrated and described as embodied in a hair treatment composition with long-lasting fixing properties, it is not intended to be limited to the details shown, since various modifications and changes may be made without departing in any way from the spirit of the present invention.

Without further analysis, the foregoing will so fully reveal the gist of the present invention that others can, by Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and is set forth in the following appended claims.

We claim:

1. A hair treatment composition comprising at least one nonionic, water-insoluble vinyl/silicone copolymer having a backbone chain of siloxane polymer units and a side chain of vinyl polymer units, and at least one polydimethylsiloxane with hydroxy end groups.

2. The hair treatment composition as defined in claim 1, wherein said at least one vinyl/silicone copolymer has the formula (I):

$$R^1R^2R^3Si\text{---}[O\text{---}SiR^4R^5\text{---}]_nO\text{---}SiR^6R^7R^8 \qquad (I),$$

wherein the $R^1$ to $R^8$ groups are the same or different and, independently from each other, are each hydrogen, a hydroxy group, an alkyl group, an aryl group, an alkylaryl group, an alkoxy group, an alkylamino group, a fluoroalkyl group or a ZSA group, wherein Z represents an alkylene group having from 1 to 10 carbon atoms, an alkarylene group having from 1 to 10 carbon atoms, an arylene group having from 1 to 10 carbon atoms or an alkoxyalkylene group having 1 to 10 carbon atoms; S represents sulfur; A is a vinyl polymer segment built up from nonionic monomer units and n is a number not less than 5; with the proviso that at least one of the $R^1$ to $R^8$ groups is one of the ZSA groups.

3. The hair treatment composition as defined in claim 2, wherein said Z represents a methylene group or a propylene group and wherein said vinyl polymer units are selected from the group consisting of esters of acrylic acid and alcohols having from 1 to 18 carbon atoms and esters of methacrylic acid and alcohols having from 1 to 18 carbon atoms.

4. The hair treatment composition as defined in claim 1, wherein said at least one vinyl/silicone copolymer is a dimethylsiloxane/methyl-3-mercaptopropylsiloxane/isobutylmethacrylate copolymer.

5. The hair treatment composition as defined in claim 1, wherein said at least one vinyl/silicone copolymer is present in an amount of from 0.1 to 50 percent by weight and said at least one polydimethylsiloxane with hydroxy end groups is present in an amount of from 0.01 to 50 percent by weight.

6. The hair treatment composition as defined in claim 1, further comprising at least one volatile silicone compound.

7. The hair treatment composition as defined in claim 6, wherein said at least one volatile silicone compound is selected from the group consisting of volatile linear polydimethylsiloxanes groups and volatile cyclic polydimethylsiloxanes.

8. The hair treatment composition as defined in claim 1, further comprising at least one film-forming, hair-fixing synthetic or natural polymer.

9. A hair treatment composition comprising at least one nonionic, water-insoluble vinyl/silicone copolymer having a backbone chain of siloxane polymer units and a side chain of vinyl polymer units, and at least one polydimethylsiloxane with hydroxy end groups, wherein said at least one vinyl/silicone copolymer has the formula (I):

$$R^1R^2R^3Si\text{---}[O\text{---}SiR^4R^5\text{---}]_nO\text{---}SiR^6R^7R^8 \qquad (I),$$

wherein the $R^1$ to $R^8$ groups are the same or different and, independently from each other, are each hydrogen, a hydroxy group, an alkyl group, an aryl group, an alkylaryl group, an alkoxy group, an alkylamino group, a fluoroalkyl group or a ZSA group, wherein Z represents an alkylene group having from 1 to 10 carbon atoms, an alkarylene group having from 1 to 10 carbon atoms, an arylene group having from 1 to 10 carbon atoms or an alkoxyalkylene group having 1 to 10 carbon atoms; S represents sulfur; A is a vinyl polymer segment built up from nonionic monomer units and n is a number not less than 5; with the proviso that at least one of the $R^1$ to $R^8$ groups is one of the ZSA groups.

10. The hair treatment composition as defined in claim 9, wherein said at least one vinyl/silicone copolymer is a dimethylsiloxane/methyl-3-mercaptopropylsiloxane/isobutylmethacrylate copolymer.

11. The hair treatment composition as defined in claim 9, comprising from 0.1 to 50 percent by weight of said at least one vinyl/silicone copolymer; from 0.01 to 50 percent by weight of said at least one polydimethylsiloxane with hydroxy end groups, and wherein said polydimethylsiloxane with hydroxy end groups has a viscosity less than 100,000 mPa.s at 25° C.; and from 5 to about 90 percent by weight of at least one solvent selected from the group consisting of water and alcohols having 1 to 4 carbon atoms.

12. The hair treatment composition as defined in claim 11, further comprising from 0.01 to 50 percent by weight of at least one synthetic or natural film-forming hair-fixing polymer.

* * * * *